(12) United States Patent
Kim et al.

(10) Patent No.: US 7,427,687 B2
(45) Date of Patent: Sep. 23, 2008

(54) GLYCIDYL DINITROPROPYL FORMAL POLY (GLYCIDYL DINITROPROPYL FORMAL) AND PREPARATION METHOD THEREOF

(75) Inventors: Jin Seuk Kim, Daejeon (KR); Jin Rai Cho, Daejeon (KR); Keun Deuk Lee, Daejeon (KR); Jae Kyoung Kim, Daejeon (KR)

(73) Assignee: Agency for Defense Development, Daejeon (KR)

( * ) Notice: Subject to any disclaimer, the term of this patent is extended or adjusted under 35 U.S.C. 154(b) by 8 days.

(21) Appl. No.: 11/682,806

(22) Filed: Mar. 6, 2007

(65) Prior Publication Data

US 2008/0039610 A1  Feb. 14, 2008

Related U.S. Application Data

(63) Continuation of application No. 10/830,973, filed on Apr. 22, 2004, now Pat. No. 7,208,637.

(30) Foreign Application Priority Data

Apr. 30, 2003  (KR)  ................ 2003-27807

(51) Int. Cl.
*C07D 303/08* (2006.01)
(52) U.S. Cl. .................................... 549/551
(58) Field of Classification Search ............ 549/551
See application file for complete search history.

(56) References Cited

U.S. PATENT DOCUMENTS 6,909,100 B2 *  6/2005  Sognefest et al. ...... 250/370.13

\* cited by examiner

*Primary Examiner*—Rebecca L Anderson
*Assistant Examiner*—Shawquia Young
(74) *Attorney, Agent, or Firm*—Jeffrey J. King

(57) ABSTRACT

Disclosed are novel compounds that can be used as an energetic binder used for improving the performance and the properties of a high explosive, and a preparation method thereof. More specifically, provided are glycidyl dinitropropyl formal of chemical formula IV having a nitro group ($-NO_2$) as an energy group and having no hydrogen bonding to carbon to which the nitro group is binding, poly(glycidyl dinitropropyl formal) of chemical formula V polymerized using the glycidyl dinitropropyl formal as a monomer, and a preparation method thereof.

1 Claim, 1 Drawing Sheet

GLYCIDYL DINITROPROPYL FORMAL POLY (GLYCIDYL DINITROPROPYL FORMAL) AND PREPARATION METHOD THEREOF

RELATED APPLICATIONS

This is a CONTINUATION of the prior application Ser. No. 10/830,973, filed Apr. 22, 2004, now U.S. Pat. No. 7,208,637 which is entiled to priority benefit of Korean Patent Application No. KR 27807/2003, filed Apr. 30, 2003, each of which priority disclosures is incorporated herein by reference.

FIELD OF THE INVENTION

The present invention relates to a synthesis of an energetic prepolymer used as a high-energy binder for an insensitive and high performance explosive.

DESCRIPTION OF THE BACKGROUND ART

Currently, HTPB (Hydroxyl-Terminated Polybutadiene), a prepolymer for a binder for Plastic-Bonded Explosives (PBX's) is being widely used as a binder for polyurethane groups. This binder is included in PBX in the amount of about 15% to improve mechanical properties of PBX's. However, this binder is an inert material, and thereby causing reduction of energy of PBX's. Therefore, many efforts are made to develop a high-energy contained binder (an energetic binder) for increasing the energy of PBX's.

As a result of such efforts, various energetic binders have been developed such as PNG [poly (glycidyl nitrate)] as expressed as the following chemical formula 1, PNMMO [poly(3-nitratomethyl-3-methyloxetane)], and the like. However, the above prepolymers show poor thermal stabilities, since they contain nitrate groups as an energy group, whereby the thermal decomposition onset temperature appears at about 180° C. Especially, as shown in reaction scheme 1, the PGN is self-decomposed in a polyurethane elastomer when the polyurethane elastomer is synthesized.

Chemical Formula 1

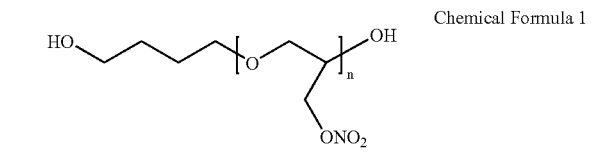

n = 10~40

Reaction Scheme 1

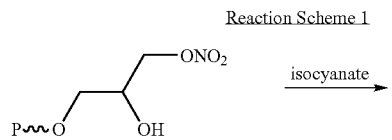

-continued

As shown in reaction scheme 1, when the polyurethane elastomer is synthesized by using PGN of chemical formula 1, hydrogen bonding to carbon to which a nitrate group binds is chemically acidified thus to easily cause a decomposition reaction as shown in reaction scheme 1, thereby causing a decomposition of the main chain of polyurethane. Nevertheless, since the PGN has been known as a material having the best performance among existing energetic prepolymers, many researches are made in order to solve such problems. However, outstanding results have not been obtained yet.

SUMMARY OF THE INVENTION

Therefore, in the present invention, in order to improve the thermal stability of the energetic binder, a nitro group is introduced instead of the nitrate group. Further, in order to solve a self-decomposition problem in the conventional polyurethane binder prepared by using PGN, the present invention provides a compound having no hydrogen bonding to carbon to which the nitro group binds. The present invention introduces the nitro group instead of the nitrate group, and thereby enables to provide a prepolymer having an improved thermal stability compared with that of the conventional energy binder. Moreover, the present invention uses inexpensive initiating and intermediate materials and can achieve a high yield of the product, thus to be advantageous in the economical aspect.

The foregoing and other objects, features, aspects and advantages of the present invention will become more apparent from the following detailed description of the present invention when taken in conjunction with the accompanying drawings.

BRIEF DESCRIPTION OF THE DRAWINGS

The accompanying drawings, which are included to provide a further understanding of the invention and are incorporated in and constitute a part of this specification, illustrate embodiments of the invention and together with the description serve to explain the principles of the invention.

In the drawings.

DETAILED DESCRIPTION OF THE PREFERRED EMBODIMENTS

Figure 1:
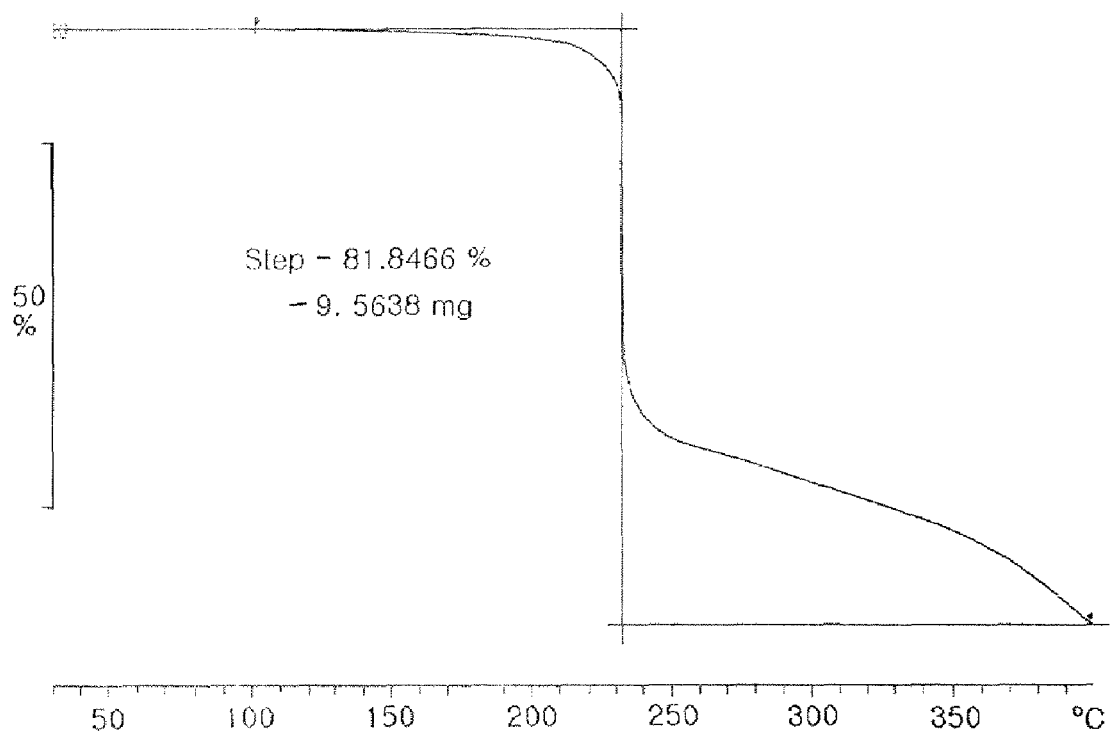
FIG. 1 shows an experimental result for the thermal stability of poly(glycidyl dinitropropyl formal) according to the present invention.

Reference will now be made in detail to the preferred embodiments of the present invention, examples of which are illustrated in the accompanying drawings.

The present invention provides novel compounds for use in an energetic binder for improving the performance and properties of a high explosive. More particularly, the present invention provides glycidyl dinitropropyl formal having a nitro group as an energy group, having no hydrogen bonding to carbon to which the nitro group binds, as expressed by chemical formula IV, poly(glycidyl dinitropropyl formal) polymerized by using the glycidyl dinitropropyl formal as a monomer, as expressed by chemical formula V, and a preparation method thereof.

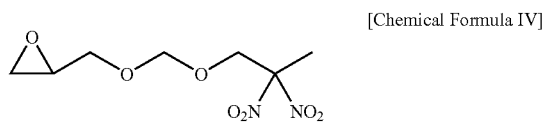

[Chemical Formula IV]

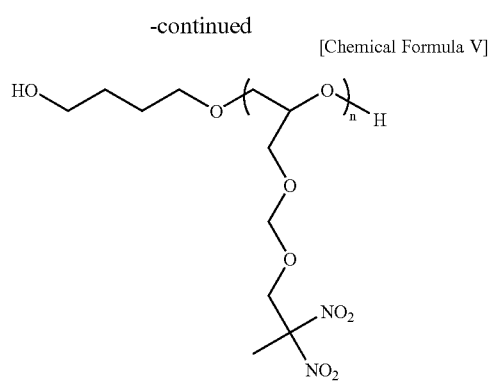

[Chemical Formula V]

$n = 10\sim40$ in the present invention, the novel compound, glycidyl dinitropropyl formal of chemical formula IV, is used as a monomer for synthesizing the novel compound, poly(glycidyl dinitropropyl formal) of chemical formula V. Poly(glycidyl dinitropropyl formal) of chemical formula V is very useful as an energetic prepolymer due to an excellent thermal stability and a characteristic that it is not self-decomposed in synthesizing a polyurethane elastomer. The existing energetic prepolymer contains a nitrate group having a low thermal stability as an energy group, and thereby has a low thermal stability. However, an energetic binder prepared by the compound of the present invention containing a nitro group as an energy group has an improved thermal stability compared with that of the existing energetic prepolymer. Further, the present invention uses inexpensive initiating and intermediate materials and can achieve a high yield of the product, thus to be very economical.

A process for synthesizing glycidyl dinitropropyl formal of chemical formula IV and poly(glycidyl dinitropropyl formal) of chemical formula V is shown in the following reaction scheme 2.

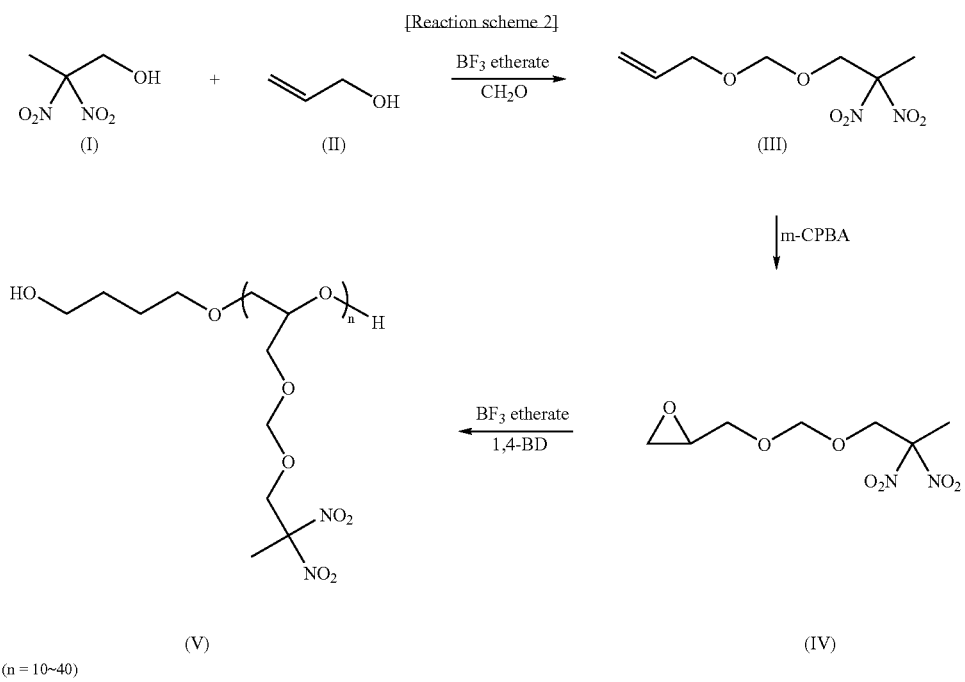

[Reaction scheme 2]

Said reaction scheme will be explained in more detail as follows.

Firstly, 2,2-dinitripropanol (DNP-OH) of chemical formula I and allyl alcohol of chemical formula II are reacted with boron trifluoride etherate to obtain allyl 2,2-dinitropropyl formal (ADNPF) of chemical formula III (Reaction scheme 2-1).

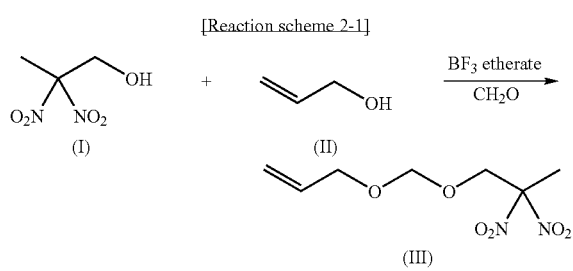

Then, the obtained allyl 2,2-dinitropropyl formal (ADNPF) is reacted with metha-chloroperbenzoic acid (m-CPBA) to obtain glycidyl dinitropropyl formal of chemical formula IV (Reaction scheme 2-2).

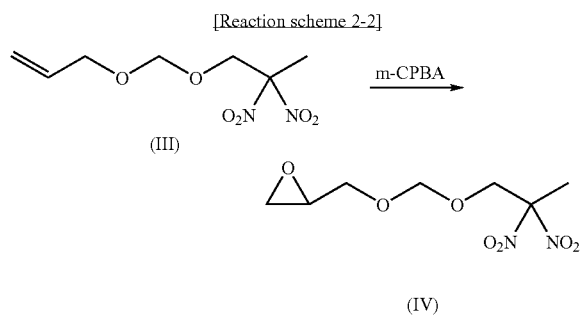

The obtained glycidyl dinitropropyl formal is polymerized in a mixed solution of boron trifluoride etherate and 1,4-butandiol (1,4-BD), to obtain poly(glycidyl dinitropropyl formal) of chemical formula V (Reaction scheme 2-3).

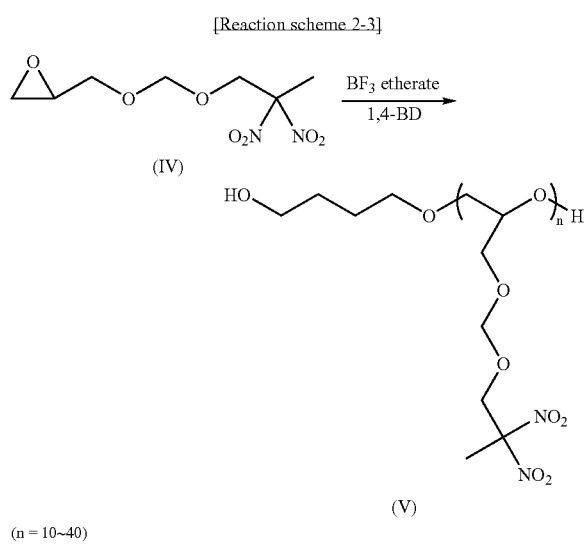

The obtained poly(glycidyl dinitropropyl formal) has an excellent thermal stability and does not include unstable hydrogen group thus not to cause a self-decomposition when preparing a polyurethane elastomer, thereby being very useful as a new energetic prepolymer that can be used as an energetic binder for an insensitive and high performance explosive.

Hereinafter, the present invention will be explained in more detail with reference to preferred examples.

EXAMPLE 1

Synthesis of Allyl Dinitropyl Formal (ADNPF)

15 g (0.1 mol) of 2,2-dinitropropanol (DNP-OH) of chemical formula I, 3.3 g (0.11 mol) of formaldehyde and a desired amount (wherein the equivalent is controlled) of allyl alcohol of chemical formula II were put in a 250 ml 3-necks round bottom flask equipped with a thermometer and a dropping funnel and 40 g of methylene chloride (MC) in which moisture has been removed was put therein. The temperature of the solution was lowered to 5° C. or below, and 42.6 g (0.3 mol) of boron trifluoride etherate was slowly injected thereto with maintaining the temperature of the reaction solution at 5° C. After injection, the solution was strongly stirred with maintaining the temperature of the solution at 5° C. or below for approximately 40 minutes, and then the reaction was completed.

After the reaction, 100 ml of distilled water was slowly added to the reaction mixture, stirred, and phase-separated in the separating funnel. An organic layer was washed with 5% caustic soda solution three times, with distilled water one time, with sodium chloride solution one time, and then with distilled water one time. Then, the resulting product was dried with anhydrous magnesium sulfate and the solvent was removed, to obtain allyl dinitropropyl formal of chemical formula III.

NMR (CDCl$_3$, δ for TMS); 2.18 (s, 3H), 4.0 (d, 2H), 4.33 (s, 2H), 4.71 (s, 2H), 5.2 (m, 2H), 5.8 (m, 1H)

Herein, a yield of the allyl dinitropropyl formal (AN\DNPF) becomes different depending on the reaction condition, and a result depending on a composition ratio between alcohols was shown in the following table 1. In order to obtain allyl dinitropropyl formal of a high purity, a fractional distillation was performed using a Thin Film Evaporator (TFE, a capacity: 1 L, Pope) with setting a temperature of an outer wall as 100° C.

TABLE 1

| DNP-OH:allyl alcohol (mol ratio) | Crude yield of ADNPF (%) | Concentration of ADNPF (Result of GC analysis, %) | Final yield of ADNPF |
|---|---|---|---|
| 1:3 | 94.4 | 78.0 | 73.6 |
| 1:2 | 86.1 | 75.0 | 64.6 |
| 1:1 | 79.2 | 67.0 | 53.1 |

Chemical Formula I: 2,2-dinitropropanol

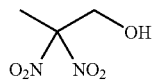
(I)

Chemical Formula II: allyl alcohol

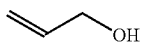
(II)

Chemical Formula III: allyl dinitropropyl formal

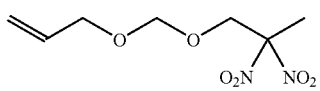
(III)

EXAMPLE 2

Synthesis of Glycidyl dinitropropyl formal (GDNPF)

33 g (0.15 mol) of allyl dinitropropyl formal and 400 g of chloroform were put into a 1-neck round bottom flask of 1 L equipped with a thermometer and a reflux condenser. Then, 45 g (0.18 mol) of meta-chloroperbenzoic acid (m-CPBA) was injected thereto through approximately 30 minutes. Since an exothermic reaction may occur when m-CPBA is poured at one time, m-CPBA was slowly injected thereto. After injecting all the m-CPBA, the temperature of the flask was slowly raised to a reflux temperature of the solvent, and then the reaction solution was strongly stirred for about 3 hours. After three hours, the heating was stopped and a reaction was performed at the normal temperature for 12 hours.

After completing the reaction, the reaction was lowered to 0° C. or below, and metha-chlorobenzoic acid (m-CBA) produced from the reaction and non-reacted m-CPBA were filtered as a solid crystal and extracted. Then, the solution was washed two times with 5% sodium sulfite, and was sufficiently washed with 5% sodium hydroxide until m-CBA is completely removed. The solution was washed one time with saturated sodium chloride solution, dried with anhydrous magnesium sulfate, and filtrated. Then, the solvent was removed, volatile matters were completely removed by a vacuum pump, and impurities were removed by using a thin film evaporator at 90° C., to obtain 32.56 g of glycidyl dinitropropyl formal of chemical formula IV (yield: 92%).

NMR (CDCl$_3$, δ for TMS); 2.17 (s, 3H), 2.60 (t, 1H), 2.78 (t, 1H), 3.1 (m, 1H), 3.8 (m, 1H), 4.3 (s, 2H), 4.7 (s, 2H)

Chemical Formula IV: glycidyl dinitropropyl formal (GDNPF)

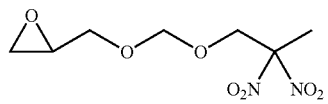

PREFERRED EMBODIMENT 3

Synthesis of Poly(glycidyl dinitropropyl formal) [p(GDNPF)]

0.18 g (2 mmol) of 1,4-butandiol was added to 28 g (1 mmol) of boron trifluoride etherate, then ether was completely removed by decompression for approximately 2 hours, and then 12 g of methylene chloride (MC) was added thereto. 11.5 g (50 mmol) of the glycidyl dinitropropyl formal obtained in example 2, which was dissolved in methylene chloride, was injected to the reaction solution for approximately three hours.

After injection, the resulting solution was additionally reacted for 30 minutes to complete a polymerization reaction. Then, the solution was washed with 50 ml of water and 30 ml of methylene chloride. Next, the solution was washed three times with 50 ml of saturated sodium chloride solution, and then dehydrated by anhydrous magnesium sulfate. Then, 20 ml of ethanol was added to the obtained polymer and the reaction mixture was stirred to wash out the non-reacted organic material. The pressure was reduced at 1 mmHg/80° C. for 5 hours to completely remove volatile matters. A prepolymer poly(glycidyl dinitropropyl formal) of chemical formula V having a numeric average molecular weight of 2,200, a polydispersity of 1.12, a hydroxyl group of 0.621 eq/kg, a glass transition temperature of −23° C., and a thermal decomposition initiating temperature of 200° C. or more was obtained with the yield of about 90%.

Chemical Formula V: Poly(glycidyl dinitropropyl formal)

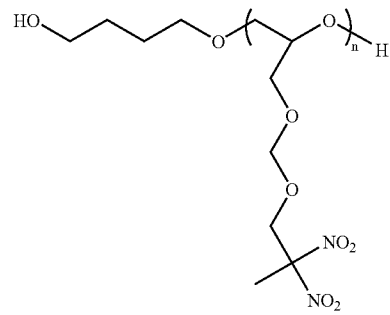

n = 10~40

EXAMPLE 4

Thermal Decomposition property of Poly(glycidyl dinitropropyl formal)

Dissociation energy of nitro group (—NO$_2$) according to a material to which it binds was shown in the following table 2. As shown in the table 2, the dissociation energy of X—NO$_2$ becomes greatly different according to the binding position of nitro group, and appears the greatest value when the nitro group bonds to carbon. Accordingly, it can be predicted that a compound in which a nitro group is bonding to carbon like in the present invention has a high thermal stability (Jimmie C. Oxley, James L. Smith, and ZunLiang Zhou, J. Phys. Chem., 99, 10383-10391, 1995).

TABLE 2

| Dissociation energy of X—$NO_2$ according to the binding material(X) | |
|---|---|
| X | Dissociation energy (kcal/mol) |
| O | 40 |
| N | 47 |
| C | 70 |

The thermal decomposition property of poly(glycidyl dinitropropyl formal) prepared in example 3 was shown in FIG. 1. For the test of thermal decomposition property, a loss weight of poly (glycidyl dinitropropyl formal) by being decomposed was measured by raising the temperature from normal temperature at the rate 10° C./min using the TGA (Mettler company) in the manner of being conventionally used in the related art. As shown in FIG. 1, poly(glycidyl dinitropropyl formal) according to the present invention is thermally stable even at the temperature of 200° C. or more.

The present invention relates to a novel compound that can be used as an energetic binder for improving the performance and the property of a high explosive. The existing energetic binders have shown a low thermal stability due to containing a nitrate group having a low thermal stability as an energy group. However, the energetic binder prepared using the compound of the present invention containing a nitro group as an energy group shows a improved thermal stability compared with the existing energetic binders. Further, the compounds of the present invention are not self-decomposed, and thus, they are very useful as an energetic prepolymer used as a energetic binder and a monomer thereof. Additionally, the present invention uses an inexpensive initiating material and intermediate material and achieves a high yield, thereby being economical.

As the present invention may be embodied in several forms without departing from the spirit or essential characteristics thereof, it should also be understood that the above-described embodiments are not limited by any of the details of the foregoing description, unless otherwise specified, but rather should be construed broadly within its spirit and scope as defined in the appended claims, and therefore all changes and modifications that fall within the metes and bounds of the claims, or equivalence of such metes and bounds are therefore intended to be embraced by the appended claims.

What is claimed is:

1. Glycidyl dinitropropyl formal expressed as the following chemical formula IV

[Chemical Formula IV]

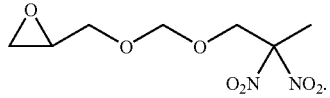

* * * * *